(12) United States Patent
Bock et al.

(10) Patent No.: US 8,871,936 B2
(45) Date of Patent: Oct. 28, 2014

(54) METHOD FOR MANUFACTURING OF QUINOLINE-3-CARBOXAMIDES

(75) Inventors: Lillemor Maria Bock, Karlskoga (SE); Par Henning Holmberg, Karlskoga (SE); Karl-Erik Jansson, Dalby (SE)

(73) Assignee: Active Biotech AB, Lund (SE)

( * ) Notice: Subject to any disclaimer, the term of this patent is extended or adjusted under 35 U.S.C. 154(b) by 0 days.

(21) Appl. No.: 13/809,233

(22) PCT Filed: Jul. 7, 2011

(86) PCT No.: PCT/EP2011/061490
§ 371 (c)(1),
(2), (4) Date: Jan. 9, 2013

(87) PCT Pub. No.: WO2012/004338
PCT Pub. Date: Jan. 12, 2012

(65) Prior Publication Data
US 2013/0109860 A1     May 2, 2013

Related U.S. Application Data

(60) Provisional application No. 61/362,849, filed on Jul. 9, 2010.

(30) Foreign Application Priority Data

Jul. 9, 2010  (EP) .................................... 10169162

(51) Int. Cl.
*C07D 215/56*     (2006.01)

(52) U.S. Cl.
CPC .................................. *C07D 215/56* (2013.01)
USPC ...................................................... 546/155

(58) Field of Classification Search
None
See application file for complete search history.

(56) References Cited

U.S. PATENT DOCUMENTS

| 3,868,379 A | 2/1975 | Zinnes et al. |
| 5,912,349 A | 6/1999 | Sih |
| 6,077,851 A | 6/2000 | Bjork et al. |
| 6,133,285 A | 10/2000 | Bjork et al. |
| 6,875,869 B2 | 4/2005 | Jansson |
| 7,560,557 B2 * | 7/2009 | Jansson .......................... 546/155 |
| 2011/0105756 A1 * | 5/2011 | Dixit et al. .................... 546/155 |

FOREIGN PATENT DOCUMENTS

CN     1298393 A     6/2001

OTHER PUBLICATIONS

Roelofsen, D.P., Molecular Sieve Zeolites—Properties & Applications in Organic Synthesis (1972).*
Ten Haken: "Use of molecular sieves for affecting the equilibrium of reactions", Chemistry & Industry, Society of Chemical Industry, London, GB, No. 7, 1973, p. 325, XP008130938, ISSN: 0009-3068 the whole document.
Johan Wennerberg et al.: "Development of a Practical and Reliable Synthesis of Laquinimod" Organic Process Research & Development, 674-680, vol. 11, No. 4, 2007, American Chemical Society.
Stig Jonsson et al. "Synthesis and Biological Evaluation of New 1,2-Dihydro-4-hydroxy-2-oxo-3-quinolinecarboxamides for Treatment of Autoimmune Disorders: Structure-Activity Relationship" J. Med. Chem. 2004, 47, 2075-2088, Active Biotech Research AB, Box 724, SE-220 07 Lund, Sweden, Received Sep. 23, 2003.
Lu Jin et al.: "Computational Study on the Aminolysis of β-Hydroxy-α,β-Unsaturated Ester via the Favorable Path Including the Formation of α-Oxo Ketene Intermediate", J. Phys. Chem. A 2008, 112, 4501-4510, Received: Jul. 18, 2007; Revised Manuscript Received: Dec. 29, 2007.
Karl Jansson et al. "Synthesis and Reactivity of Laquinimod, a Quinoline-3-carboxamide: Intramolecular Transfer of the Enol Proton to a Nitrogen Atom as a Plausible Mechanism for Ketene Formation", R&D Laboratories, Active Biotech Research AB, Box 724, SE-220 07 Lund, Sweden, Received Nov. 16, 2005, J. Org. Chem. 2006, 71, 1658-1667.
International Search Report, dated Oct. 27, 2011, from corresponding PCT application.

* cited by examiner

*Primary Examiner* — Janet L Andres
*Assistant Examiner* — Timothy R Rozof
(74) *Attorney, Agent, or Firm* — Young & Thompson

(57) ABSTRACT

A method for preparing a compound of formula (I) by reacting the appropriate alkyl ester and an aniline derivative, in a refluxing mixture containing an aliphatic solvent or a mixture of aliphatic solvents having a boiling point in the range of 68-191° C.; condensing vapors of the refluxing mixture; treating the condensed vapors with an alcohol scavenging agent or a mixture of alcohol scavenging agents; and returning the condensed vapors back to the reaction mixture.

18 Claims, 2 Drawing Sheets

METHOD FOR MANUFACTURING OF QUINOLINE-3-CARBOXAMIDES

FIELD OF THE INVENTION

The present invention relates to the field of organic synthesis. In particular, it relates to the field of chemical synthesis of certain derivatives of N-alkyl-N-phenyl-quinoline-3-carboxamides.

BACKGROUND OF THE INVENTION

N-alkyl-N-phenyl-quinoline-3-carboxamides are a promising class of compounds being evaluated in clinical trials against different classes of diseases, e.g. autoimmune diseases and cancer.

N-alkyl-N-phenyl-quinoline-3-carboxamides such as paquinimod (herein below also referred to as A), laquinimod (herein below also referred to as B), and tasquinimod (herein below also referred to as C), have been prepared by a method involving distillation of the volatiles from a mixture comprising an ester, aniline and an aliphatic solvent such as n-heptane or n-octane.

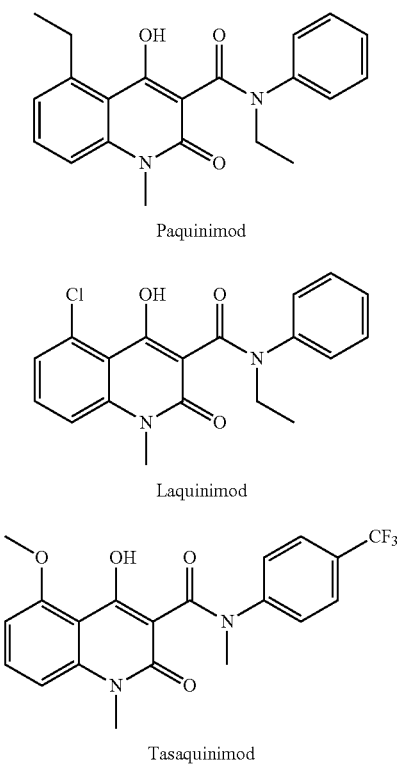

This method is described in U.S. Pat. No. 6,875,869.

The prior art synthetic protocol (Org. Process. Res& Dev. 2007, 11, 674-680) for N-alkyl-N-phenyl-quinoline-3-carboxamides such as paquinimod (A), laquinimod (B), and tasquinimod (C) is exemplified with synthesis of paquinimod in Scheme 1. The route starts with an anthranilic acid 1 which is transformed into an isatoic anhydride 2. The isatoic anhydride is methylate to give 3, which is condensed with dimethylmalonate to give the corresponding methyl ester 4. The methyl ester is subsequently condensed with the appropriate aniline, to give the desired final compound.

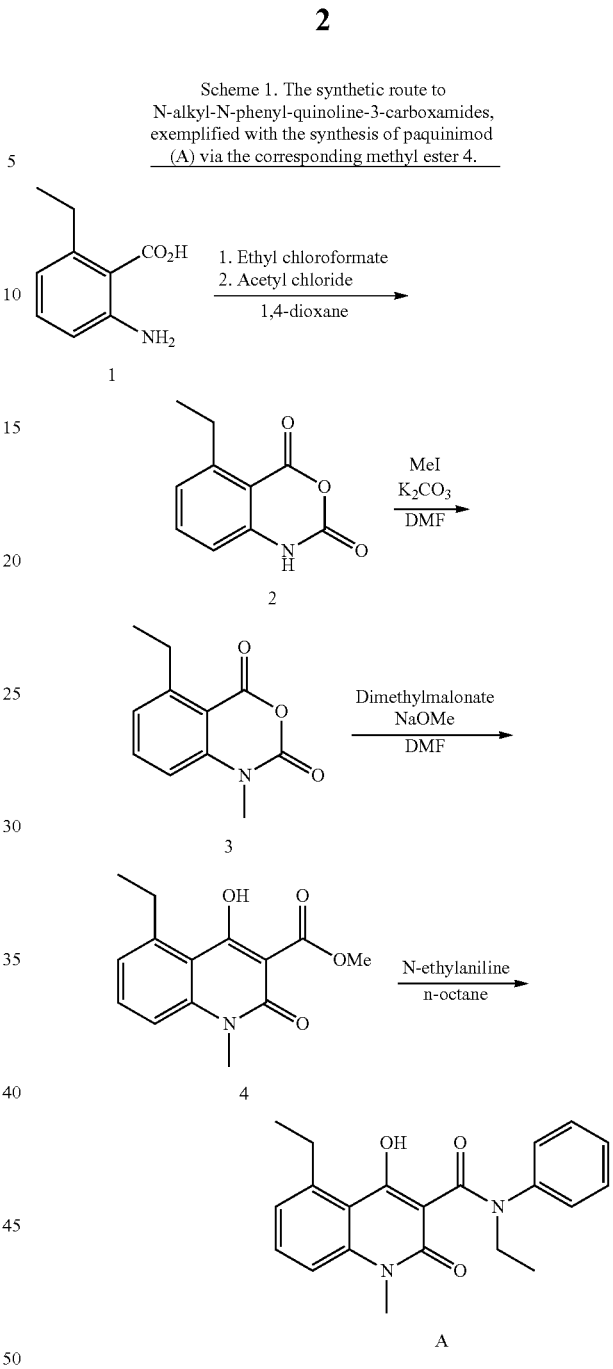

This manufacturing method is short and avoids the use of expensive reagents. All intermediates are stable and easy to isolate in high purity by precipitation and filtration. The main impurity in the final condensation step is remaining alkyl ester. Alternative methods, such as carbodiimide mediated coupling between a carboxylic acid and aniline, or the condensation of N-alkyl-N-phenyl-malonamic acid methyl ester with an isatoic anhydride (U.S. Pat. No. 5,912,349) are either longer or yield product of lower purity.

The final condensation step is an equilibrium (Scheme 2) that favors the alkyl ester and a reaction mechanism involving a ketene intermediate 5 has been strongly indicated (J. Org. Chem. 2006, 71, 1658-1667 and J Phys. Chem. A 2008, 112, 4501-4510).

Scheme 2. An intermediate ketene 5 is involved in the equilibrium between 4 and A.

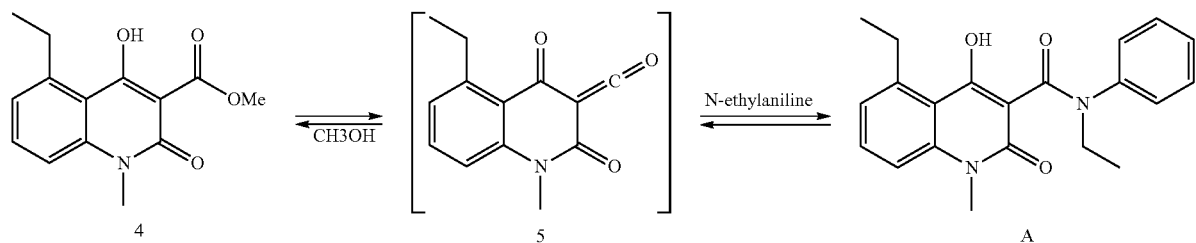

Usually formation of amides from esters and anilines requires very high reaction temperatures that also cause extensive byproduct formation. The above-mentioned reaction is enabled at moderate temperatures by the ability of 4 to unimolecularly form the ketene intermediate 5 instead of a tetrahedral intermediate. The method, which is described e.g. in U.S. Pat. No. 6,875,869, comprises charging the reactor with an appropriate ester and an aniline derivative in an aliphatic solvent such as n-heptane or n-octane. The equilibrium is driven towards the desired product by distilling off the solvent and any formed alcohol. After complete reaction the mixture is cooled and the precipitated raw product is isolated by filtration.

Unlike most other reactions where esters are transformed into thermodynamically more stable amides this particular reaction needs a very efficient removal of formed alcohol in order to give a high yield.

The method described above has been used for GMP (Good Manufacturing Practice) manufacturing of paquinimod, laquinimod and tasquinimod.

SUMMARY OF THE INVENTION

As noted herein above, in the reaction described in Org. Process. Res& Dev. 2007, 11, 674-680 for preparing an N-alkyl-N-phenyl-quinoline-3-carboxamide, the main impurity in the isolated raw product is the alkyl ester, used as the starting material in the final condensation step. This condensation may be represented by to the following general reaction scheme:

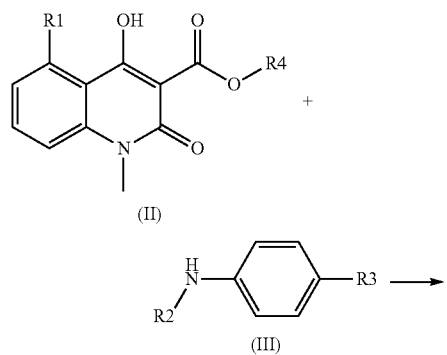

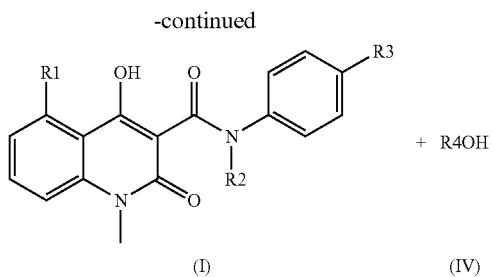

In the reaction as represented herein above, the remaining ester (II) may be easily removed from the product by recrystallisation, if small amounts of the ester are present. On the other hand, the present inventors have discovered that if larger amounts of remaining ester are present in the raw product, only one recrystallisation may not be enough for achieving a pure product. It is therefore important to drive the equilibrium as far as possible to the product side, by removal of the alcohol (IV) that is formed as a byproduct in the reaction.

The present inventors also have discovered, as a further problem, that the removal of the alcohol (IV) is scale-dependent. Thus, when the condensation reaction is performed on a small scale (e.g. less than 20 g), most of the ester (II) is transformed into product (I) within a few hours of distillation. In this case, the precipitated product contains only low, and acceptable, amounts of the ester as an impurity. However, on a larger scale, e.g. kilogram scale, the process becomes less predictable and in some cases a substantial amount of the ester (II) still persists in the mixture even after 20 hours of distillation. In such cases more solvent has to be added and the distillation continued until most of the ester (II) is transformed into the desired product (I). A process that consumes large and unpredictable amounts of the aliphatic solvent in order to get full conversion is far from optimal for drug manufacturing.

The present inventors therefore set out to solve the problem of providing an improved method for preparing a compound of formula (I), as defined herein, in a high yield, advantageously without the above-mentioned drawbacks. In particular, this method should allow preparing the compound according to formula (I) on a large scale in high yield and in high purity, advantageously without the need for prolonged reaction times and excessive solvent and energy consumption.

Accordingly, a method is provided for preparing a compound of formula (I)

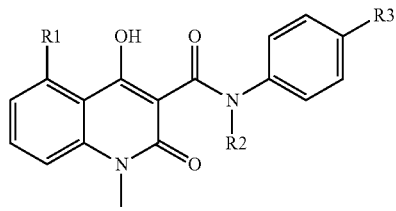

wherein
R1 is ethyl, R2 is ethyl and R3 is H; or
R1 is chloro, R2 is ethyl and R3 is H; or
R1 is methoxy, R2 is methyl and R3 is trifluoromethyl;
by
(i) reacting a compound of formula (II)

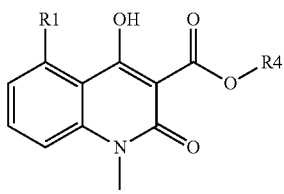

wherein
R1 is ethyl, chloro or methoxy; and
R4 is C1-C4 alkyl;
with a compound of formula (III)

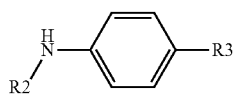

wherein
R2 is ethyl and R3 is H; or
R2 is methyl and R3 is trifluoromethyl;
in a refluxing mixture containing an aliphatic solvent or a mixture of aliphatic solvents, said aliphatic solvent(s) having a boiling point in the range of 68-191° C.;
(ii) condensing vapors of the refluxing mixture;
(iii) treating the condensed vapors with an alcohol scavenging agent or a mixture of alcohol scavenging agents; and
(iv) returning the condensed vapors back to the reaction mixture.

The present inventors have found that by the method as defined herein, a higher reaction yield may be obtained in a shorter reaction time, compared to the prior art methods. This in turn results in reduced energy consumption, which in addition to a reduced solvent consumption during the reaction, is very advantageous from an economic and environmental point of view. Furthermore, by the method of the present invention, a reaction product of a higher purity is obtainable. Very advantageously, a reaction product at a higher yield and improved purity is obtained in a shorter reaction time and at a lower solvent and energy consumption than according to the prior art methods, in particular when performing the reaction on a large scale.

Other benefits of the present invention are that the use of an alcohol scavenging agent enables a higher distillation rate without reducing the reaction volume, thus a shorter reaction time is obtained; the solvent consumption is decreased to a minimum, by recycling the solvent; there is no need for careful monitoring of the distillation rate and there is an almost complete conversion of the ester, resulting in higher purity of the isolated product.

DETAILED DESCRIPTION OF THE INVENTION

The Alcohol Scavenging Agent

Figure 1:
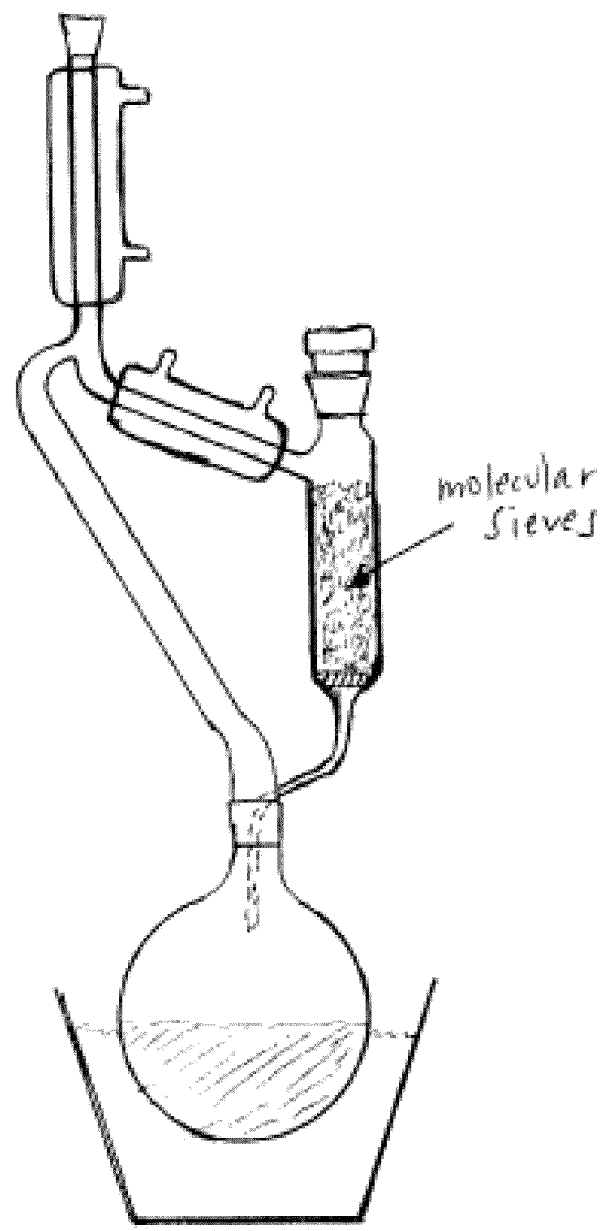
FIG. 1 represents the modified Soxhlet-apparatus used in the experiments for the evaluation of scavenging agents.

In the method of the present invention, the distillate is treated with an alcohol scavenging agent before being recycled back to the reaction mixture. The alcohol scavenging agent may be selected e.g. from molecular sieves, silica gel, and calcium chloride dihydrate or a mixture of any of these.

The present inventors have tested numerous alcohol scavenging agents in combination with different solvents and have found that molecular sieves are particularly useful for the manufacturing of compounds of formula (I) as defined herein.

Molecular sieves are crystalline metal alumina silicates having a three dimensional interconnecting network of silica and alumina tetrahedra. Molecular sieves are capable of adsorbing various polar compounds into the cavities formed by the network. Different qualities of molecular sieves exist, such as the powder forms of the 3 A, 4 A, 5 A and 13× sieves, which may be purchased e.g. from Sigma-Aldrich Co.

In one preferable embodiment, the alcohol scavenging agent is selected from molecular sieves or is a mixture of molecular sieves. For example, the alcohol scavenging agent may be selected from 3 A, 4 A, 5 A, 13× molecular sieves or may be a mixture of any of said molecular sieves.

The composition of the 3 A molecular sieve is approximately $0.6 K_2O:0.40 Na_2O:1 Al_2O_3:2.0\pm0.1 SiO_2:xH_2O$. This form is obtained by substituting potassium cations for the inherent sodium ions of the 4 A structure, giving a pore size of approximately 3 Å. The 3 A molecular sieve is known mainly for use in removing moisture.

The 4 A molecular sieve has a composition that is approximately $1 Na_2O:1 Al_2O_3: 2.0\pm0.1 SiO_2:xH_2O$. 4 A molecular sieve has an effective pore opening of about 4 angstroms (0.4 nm). This sieve is generally considered as a universal drying agent in polar and nonpolar media.

The 5 A molecular sieve is of the approximate composition $0.80 CaO:0.20 Na_2O:1 Al_2O_3:2.0\pm0.1 SiO_2:xH_2O$ and the pore size is about 5 Å.

The 13× molecular sieve is of the approximate composition $1 Na_2O:1 Al_2O_3: 2.8\pm0.2 SiO_2:xH_2O$. The pore size 13× molecular sieve is about 10 Å.

Other molecular sieves may equally well be used and it is contemplated that the skilled person will be able, by simple routine experimentation, to identify molecular sieves or mixture of molecular sieves that are suitable for use in the present invention. A further description of molecular sieves may be found in the book Molecular Sieves, R. Szostak, ed. Blackie Academic & Professional (ISBN 0 75140480 2).

The amount alcohol scavenging agent used in the method of the invention suitably is such that the weight ratio of alcohol scavenging agent to ester (II) is at least 1:1. Preferably, the alcohol scavenging agent is used in excess over the ester (II), e.g. at a weight ratio of alcohol scavenging agent to ester (II) of 2:1, or 3:1, or 5:1, or even higher.

The Aliphatic Solvent

The aliphatic solvent or mixture of aliphatic solvents for use in the method of the invention should have a boiling point in the range of 68-191° C., preferably 80-150° C., more preferably 95-130° C. Such solvents are, for example selected from C6-C10 branched or linear alkanes and cycloalkanes, e.g. C7 or C8 branched or linear alkanes and cycloalkanes.

For the purpose of the present invention, a C6-C10 branched or linear alkane or cycloalkane refers to an alkane or cycloalkane having in total from 6 to 10 carbon atoms.

A C7 or C8 branched or linear alkane refers to an alkane having in total 7 or 8 carbon atoms, e.g. n-heptane, n-octane, 2,2,4-trimethylpentane etc.

The cycloalkane may be mono- or polycyclic, e.g. bicyclic. Furthermore, the cycloalkane may be either unsubstituted or substituted (i.e. branched) with one or several, branched or linear, alkyl groups, it being understood that the total number of carbon atoms in the ring and any alkyl substituent, taken together, is 6 to 10, in particular 7 or 8. An example of a C10 cycloalkane is decalin (i.e. decahydronaphthalene). Examples of C7-C8 cycloalkanes are methylcyclohexane and cyclooctane.

Other isomers of alkanes and cycloalkanes, as may easily come to the mind of the skilled reader, are equally possible as long as the above-mentioned boiling point requirement is fulfilled.

In one embodiment, the aliphatic solvent is selected from n-heptane, n-octane, methylcyclohexane, 2,2,4-trimethylpentane and cyclooctane, or a mixture of any of these. In another embodiment, the solvent is selected from n-heptane and n-octane or a mixture of any of these.

The Compound of Formula (II)

In the Compound of Formula (II)

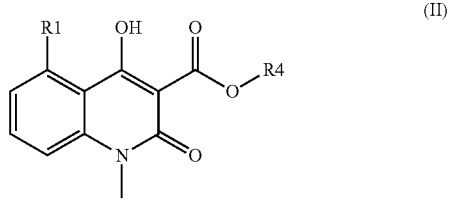

(II)

R4 is selected from C1-C4 alkyl, and may be branched or linear.

In one embodiment, R4 is selected from methyl, ethyl, n-propyl, iso-propyl and n-butyl. In another embodiment, R4 is C1-C3 alkyl, i.e. methyl, ethyl, n-propyl, and iso-propyl. In still another embodiment, R4 is methyl or ethyl, e.g. R4 is methyl.

In the condensation reaction between compounds (II) and (III), the aliphatic alcohol (IV) is formed as a byproduct and this aliphatic alcohol is withdrawn from the condensed vapors containing the aliphatic solvent or mixture of aliphatic solvents by treatment of the condensed vapors with an alcohol scavenging agent or a mixture of alcohol scavenging agents.

Some non-limiting examples of esters according to formula (II) are compounds 6-11, represented herein below.

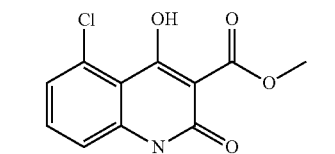

6

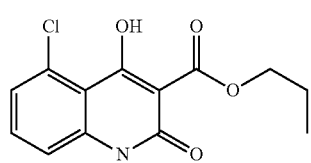

7

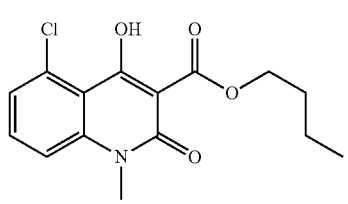

8

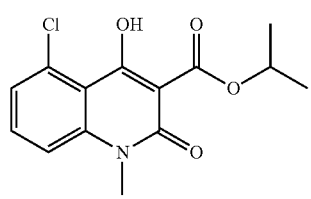

9

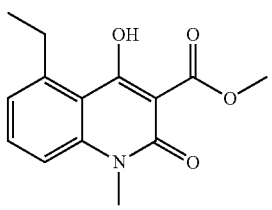

4

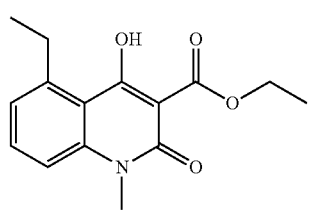

10

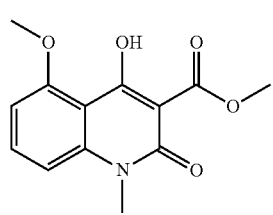

11

When using e.g. 4 as starting compound (II), the formed alcohol (IV) will be methanol, when using e.g. 10 as starting compound (II), the formed alcohol (IV) will be ethanol etc.

The Compound of Formula (I)

The product obtained in the method of the invention is a compound of formula (I),

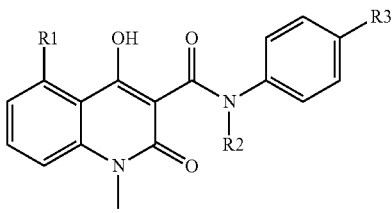

wherein
R1 is ethyl, R2 is ethyl and R3 is H; or
R1 is chloro, R2 is ethyl and R3 is H; or
R1 is methoxy, R2 is methyl and R3 is trifluoromethyl.

In one embodiment of the invention, R1 is ethyl, R2 is ethyl and R3 is H, i.e. the compound prepared is paquinimod In one other embodiment of the invention, R1 is chloro, R2 is ethyl and R3 is H, i.e. the compound prepared is laquinimod.

In still another embodiment of the invention, R1 is methoxy, R2 is methyl and R3 is trifluoromethyl, i.e. the compound prepared is tasquinimod Some Preferred Embodiments In one suitable embodiment of the invention, R1 is ethyl, R2 is ethyl, R3 is H, R4 is methyl or ethyl; the alcohol scavenging agent is a 3 A, 4 A, 5 A or 13× molecular sieve, or is a mixture thereof; and the aliphatic solvent(s) is/are selected from n-heptane and n-octane.

In one particular embodiment of the invention, R1 is ethyl, R2 is ethyl, R3 is H, R4 is methyl, the alcohol scavenging agent is a 4 A molecular sieve, and the aliphatic solvent(s) is/are selected from n-heptane and n-octane.

In another particular embodiment, R1 is ethyl, R2 is ethyl, R3 is H, R4 is ethyl, the alcohol scavenging agent is a 5 A molecular sieve, and the aliphatic solvent is n-octane.

In still another, R1 is ethyl, R2 is ethyl, R3 is H, R4 is ethyl, the alcohol scavenging agent is a 3 A molecular sieve, and the aliphatic solvent is n-octane.

In another embodiment, R1 is chloro, R2 is ethyl, R3 is H, R4 is methyl, the alcohol scavenging agent is a 3 A, 4 A, 5 A, or 13× molecular sieve, and the aliphatic solvent(s) is/are selected from n-heptane and n-octane, and in particular is n-heptane.

In one other embodiment, R1 is methoxy, R2 is methyl, R3 is trifluoromethyl, R4 is methyl or ethyl; the alcohol scavenging agent is a 3 A, 4 A, 5 A or 13× molecular sieve, or is a mixture thereof; and the aliphatic solvent is n-octane.

In one particular embodiment, R1 is methoxy, R2 is methyl, R3 is trifluoromethyl, R4 is methyl, the alcohol scavenging agent is a 4 A molecular sieve, and the aliphatic solvent is n-octane.

Herein below, the invention will be illustrated by some non-limiting examples and comparative examples, whereby the alkyl esters of formula (II), used as starting material, will be referred to by the numbering indicated herein above (i.e. compounds Nos. 4 and 6-11).

EXAMPLES

Initial experiments were conducted on a 5-gram scale using the equipment shown in FIG. 1. A special Soxhlet apparatus (not part of the invention), was designed for the evaluation. This Soxhlet apparatus cools the distillate before passing through the alcohol-scavenging material. In the classical Soxhlet apparatus the adsorption chamber has a temperature a few degrees below the boiling point of the solvent. As the experiments confirm, molecular sieves are more effective scavenging agents at lower temperatures.

In using the modified Soxhlet apparatus, the round-bottom flask is charged with ester, the appropriate aniline and a solvent. The mixture is heated to reflux and a condensate is formed in the two liquid-cooled condensers. The condensate is passed by gravity through a pad of molecular sieves and then back into the reaction mixture.

The results are summarized in Table 1. Molecular sieves are better at scavenging alcohol, e.g. methanol, at lower temperatures (Entry 17 and 20). The scavenging of alcohol from aliphatic solvents proceeded more efficiently, than if the solvent was aromatic e.g. toluene. This can be concluded from Entry 2 and 9 or Entry 17 and 21. The process was faster with molecular sieves, consumed less solvent, was easier to control and yielded a product of higher purity than the prior art method (Entry 17 and 22 or Entry 25 and 26, example 1 and 4 in experimental part, and U.S. Pat. No. 6,875,869). Methyl esters gave an excellent result with molecular sieves of the types 3 A, 4 A, 5 A, and 13× (Entry 1, 2, 4, 17, 18, 25, 27, and 28). Molecular sieves of the type 3 A and 5 A were also effective when using an ethyl ester (Entry 8 and 19). The excellent result with the condensation of a methyl or an ethyl ester (Entry 1 and 19) in the presence of 3 A molecular sieves is despite the discrepancy between the molecular size of methanol and ethanol and the 3 Angstrom cavity in the sieves. According to theory the critical diameter of methanol and ethanol respectively is too large for 3 A molecular sieves. However, 3 A molecular sieves were not effective when an n-propyl ester was used as the starting material (Entry 5). The 13× molecular sieves were effective when using an n-butyl ester in the condensation reaction (Entry 6). The molecular sieves turned out to be very effective as alcohol-scavenging material in comparison with other tested materials. Among the scavenging materials tested, calcium chloride dihydrate also gave a satisfactory result with a methyl ester but was less effective when using an ethyl ester (Entry 3 and 23). Silica gel for chromatographic purposes worked satisfactorily as an alcohol-scavenging material, but was less effective than molecular sieves (Entry 15).

TABLE 1

Evaluation of scavenging agents.

| Entry | Alkyl ester used as starting material | Conditions[a] | Product | Remaining[b] alkyl ester in product (mol %) | Yield[c] (weight %) |
| --- | --- | --- | --- | --- | --- |
| 1 | 6 | 3A MS/n-heptane/4 h | B | <1 | 95 |
| 2 | 6 | Hot 4A MS/n-heptane/4 h (classical Soxhlet) | B | <1 | 98 |

TABLE 1-continued

Evaluation of scavenging agents.

| Entry | Alkyl ester used as starting material | Conditions[a] | Product | Remaining[b] alkyl ester in product (mol %) | Yield[c] (weight %) |
|---|---|---|---|---|---|
| 3 | 6 | Calcium chloride dihydrate/n-heptane/4 h | B | 1 | 93 |
| 4 | 6 | 13X MS/n-heptane/4 h | B | <1 | 94 |
| 5 | 7 | 3A MS/n-heptane/2.5 h | B | 23 | |
| 6 | 8 | 13X MS/n-octane/2.5 h | B | <1 | 92 |
| 7 | 9 | 4A MS/n-heptane/2 h | B | 1.5 | 94 |
| 8 | 10 | 5A MS/n-octane/4 h | A | <1 | 91 |
| 9 | 6 | 4A MS/toluene/4 h | B | 12 | |
| 10 | 6 | NaOH(s)/n-heptane/4 h | B | 39 | |
| 11 | 6 | 4 h reflux in n-heptane without scavenging methanol | B | 52 | |
| 12 | 6 | Alumina/n-heptane/4 h | B | 33 | |
| 13 | 6 | Ammonium aluminum sulfate dodecahydrate/n-heptane/4 h | B | 34 | |
| 14 | 6 | Magnesiumacetate-dihydrate/n-heptane/4 h | B | 7 | |
| 15 | 6 | Silica gel 60 for chromatography | B | 3 | 95 |
| 16 | 6 | Urea/n-heptane/4 h | B | 23 | |
| 17 | 4 | 4A MS/n-heptane/2 h | A | 2 | 82 |
| 18 | 4 | 4A MS/n-octane/3.5 h | A | <1 | 89 |
| 19 | 10 | 3A MS/n-octane/2.5 h | A | <1 | 92 |
| 20 | 4 | Hot 4A MS/n-heptane/6 h (classical Soxhlet) | A | 5 | |
| 21 | 4 | 4A MS/toluene/2 h | A | 10 | |
| 22 | 4 | 2 hours distillation from n-heptane according to prior art | A | 25 | |
| 23 | 10 | Calcium chloride dihydrate/n-octane/2.5 h | A | 40 | |
| 24 | 11 | 4A MS/n-heptane/2 h | C | 87[d] | |
| 25 | 11 | 4A MS/n-octane/2 h | C | 1 | 99 |
| 26 | 11 | 2 hours distillation from n-octane according to prior art | C | 4 | 94 |
| 27 | 6 | 5A MS/n-heptane/4 h | B | <1 | 97 |
| 28 | 4 | 5A MS/n-octane/3.25 h | A | <1 | 93 |

[a]The starting material (5.0 g) and 2.0 equiv. of the appropriate aniline were suspended in the indicated solvent (150 mL) and the mixture was refluxed in the described Soxhlet-type apparatus, illustrated in FIG. 1, containing 22 gram of the alcohol-scavenging material. The mixture was then cooled and the precipitated product was isolated by filtration. In all entries the only detected impurity besides the desired product was the ester used as starting material.
[b]Remaining alkyl ester (mol %) in isolated product according to $^1$H-NMR.
[c]Isolated yields are only given when the isolated product contained less than 5% remaining starting material.
[d]Low conversion of ester is partly due to limited solubility of the starting material.

Compounds A (paquinimod), B (laquinimod), and C (tasquinimod) were described in J. Med. Chem. 2004, 47, 2075-2088. Large-scale synthesis of compound B was described in Org. Process. Res& Dev. 2007, 11, 674-680.

Compound 6 (1,2-dihydro-4-hydroxy-5-chloro-1-methyl-2-oxo-quinoline-3-carboxylic acid methyl ester) was prepared from 2-amino-6-chlorobenzoic acid according to Scheme 1 and further as described in Org. Process. Res& Dev. 2007, 11, 674-680.

$^1$H NMR (CDCl$_3$) 14.9 (s, 1H), 7.52 (t, 1H), 7.27 (m, 2H), 4.04 (s, 3H), 3.66 (s, 3H).

Compound 7 (1,2-dihydro-4-hydroxy-5-chloro-1-methyl-2-oxo-quinoline-3-carboxylic acid n-propyl ester) was prepared from compound B by refluxing in n-propanol overnight and adding dilute aqueous hydrochloric acid in order to precipitate compound 7. $^1$H NMR (CDCl$_3$) 15.06 (s, 1H), 7.50 (t, 1H), 7.27 (d, 1H), 7.23 (d, 1H), 4.39 (t, 2H), 3.64 (s, 3H), 1.87 (pentet, 2H), 1.07 (t, 3H).

Compound 8 (1,2-dihydro-4-hydroxy-5-chloro-1-methyl-2-oxo-quinoline-3-carboxylic acid n-butyl ester) was prepared from compound B by heating in n-butanol at 100° C. overnight and adding dilute aqueous hydrochloric acid and methanol in order to precipitate compound 8.

$^1$H NMR (CDCl$_3$) 15.08 (s, 1H), 7.50 (t, 1H), 7.28 (d, 1H), 7.24 (d, 1H), 4.43 (t, 2H), 3.64 (s, 3H), 1.82 (pentet, 2H), 1.52 (sextet, 2H), 0.98 (t, 3H).

Compound 4 (1,2-dihydro-4-hydroxy-5-ethyl-1-methyl-2-oxo-quinoline-3-carboxylic acid methyl ester) was prepared from 2-amino-6-ethylbenzoic acid according to Scheme 1 and further as described for compound 6 in Org. Process. Res& Dev. 2007, 11, 674-680. $^1$H NMR (CDCl$_3$) 14.9 (s, 1H), 7.57 (t, 1H), 7.22 (d, 1H), 7.08 (d, 1H), 4.06 (s, 3H), 3.68 (s, 3H), 3.27 (q, 2H), 1.31 (t, 3H).

Compound 10 (1,2-dihydro-4-hydroxy-5-ethyl-1-methyl-2-oxo-quinoline-3-carboxylic acid ethyl ester) was prepared from compound A by refluxing in ethanol overnight and adding cold dilute aqueous hydrochloric acid in order to precipitate compound 10. Compound 10 is also described in J. Med. Chem. 2004, 47, 2075-2088. $^1$H NMR (CDCl$_3$) 15.02 (s, 1H), 7.53 (t, 1H), 7.18 (d, 1H), 7.04 (d, 1H), 4.50 (q, 2H), 3.64 (s, 3H), 3.25 (q, 2H), 1.48 (t, 3H), 1.28 (t, 3H).

Compound 11 (1,2-dihydro-4-hydroxy-5-methoxy-1-methyl-2-oxo-quinoline-3-carboxylic acid methyl ester) was prepared from 2-methylamino-6-methoxybenzoic acid (U.S. Pat. No. 6,133,285) according to Scheme 1 and as described for compound 6 in Org. Process. Res& Dev. 2007, 11, 674-680. $^1$H NMR (CDCl$_3$) 13.8 (s, 1H), 7.57 (t, 1H), 6.93 (d, 1H), 6.73 (d, 1H), 4.02 (s, 3H), 4.01 (s, 3H), 3.63 (s, 3H).

Compound 9 (1,2-dihydro-4-hydroxy-5-chloro-1-methyl-2-oxo-quinoline-3-carboxylic acid isopropyl ester) was prepared from compound B by refluxing in 2-propanol overnight and adding dilute aqueous hydrochloric acid in order to precipitate compound 9. $^1$H NMR (CDCl$_3$) 15.2 (s, 1H), 7.51 (t, 1H), 7.28 (d, 1H), 7.24 (d, 1H), 5.37 (septet, 1H), 3.67 (s, 3H), 1.47 (d, 6H).

Example 1

Preparation of Compound A (Entry 17)

A mixture of 4 (5.00 g) and N-ethylaniline (4.7 g) in n-heptane (200 mL) was refluxed in a Soxhlet extraction apparatus (FIG. 1) containing 4 A molecular sieves (22.9 g). The reflux was stopped after 2.0 hours and the mixture was cooled to room temperature. The crystalline suspension was filtered. The precipitate was washed with n-heptane and dried in vacuum to furnish 5.53 g (82%) of N-ethyl-N-phenyl-5-ethyl-1,2-dihydro-4-hydroxy-1-methyl-2-oxoquinoline-3-carboxamide (A). $^1$H-NMR analysis on the isolated product revealed 2% remaining ester. $^1$H-NMR (d-DMSO), all broad peaks; 11.1 (1H), 7.41 (1H), 7.29 (2H), 7.21 (3H), 7.14 (1H), 6.96 (1H), 3.80 (2H), 3.42 (3H), 3.08 (2H), 1.07 (3H), 1.06 (3H).

When the same reaction was performed by the traditional distillation from n-heptane (Entry 22) during 2 hours according to prior art U.S. Pat. No. 6,875,869 the product was isolated in 85% yield (based on compound A) and found by $^1$H-NMR to be a mixture of compound A (75 mol %) and the ester used as starting material (25 mol %).

Example 2

Preparation of Compound B (Entry 2)

A mixture of 6 (5.00 g) and N-ethylaniline (5.0 g) in n-heptane (150 mL) was refluxed for 4.0 hours in a Soxhlet apparatus containing 4 A molecular sieves (22.9 g). After cooling the mixture the product was isolated as above to furnish 6.54 g (98%) of N-ethyl-N-phenyl-5-chloro-1,2-dihydro-4-hydroxy-1-methyl-2-oxo-quinoline-3-carboxamide (B). $^1$H-NMR analysis on the isolated product revealed no impurities. $^1$H-NMR (CDCl$_3$) 12.6 (s, 1H), 7.41 (t, 1H), 7.08-7.26 (m, 7H), 3.98 (q, 2H), 3.30 (s, 3H), 1.22 (t, 3H).

Example 3

Preparation of Compound B (Entry 3)

A mixture of 6 (5.00 g), N-ethylaniline (5.0 g) in n-heptane (150 mL) was refluxed for 4.0 hours in the Soxhlet apparatus containing calcium chloride dihydrate (flakes for drying purposes, 22.0 g). After cooling the mixture the product was isolated as above to furnish 6.20 g (93%) of N-ethyl-N-phenyl-5-chloro-1,2-dihydro-4-hydroxy-1-methyl-2-oxo-quinoline-3-carboxamide (B). $^1$H-NMR analysis on the isolated product revealed 1% remaining ester.

Example 4

Preparation of Compound C (Entry 25)

A mixture of 11 (5.00 g, 18.9 mmol), N-methyl-p-trifluoromethylaniline (5.13 g, 28.4 mmol) and n-octane (200 mL) were refluxed in a Soxhlet extraction apparatus containing 4 A molecular sieves (22.9 g) for 2 hours. After cooling the mixture the product was isolated as above to furnish 7.6 g (99%) of 4-hydroxy-5-methoxy-N,1-dimethyl-2-oxo-N-[(4-trifluoromethyl)phenyl]-1,2-dihydroquinoline-3-carboxamide (C). $^1$H-NMR analysis on the isolated product revealed no impurities other than 1 mol % remaining ester 11. $^1$H-NMR (CDCl$_3$) 9.9 (s, 1H), 7.50 (bs, 4H), 7.46 (t, 1H), 6.94 (d, 1H), 6.70 (d, 1H), 4.06 (s, 3H), 3.54 (s, 3H), 3.48 (s, 3H).

When the same reaction was performed by the traditional distillation from n-octane (Entry 26) during 2 hours according to prior art U.S. Pat. No. 6,875,869 the product was isolated in 94% yield and determined by $^1$H-NMR analysis to consist of a mixture of compound C (96 mol %) and the starting material 11 (4 mol %).

Example 5

Large-Scale Manufacturing of Compound A

Figure 2:
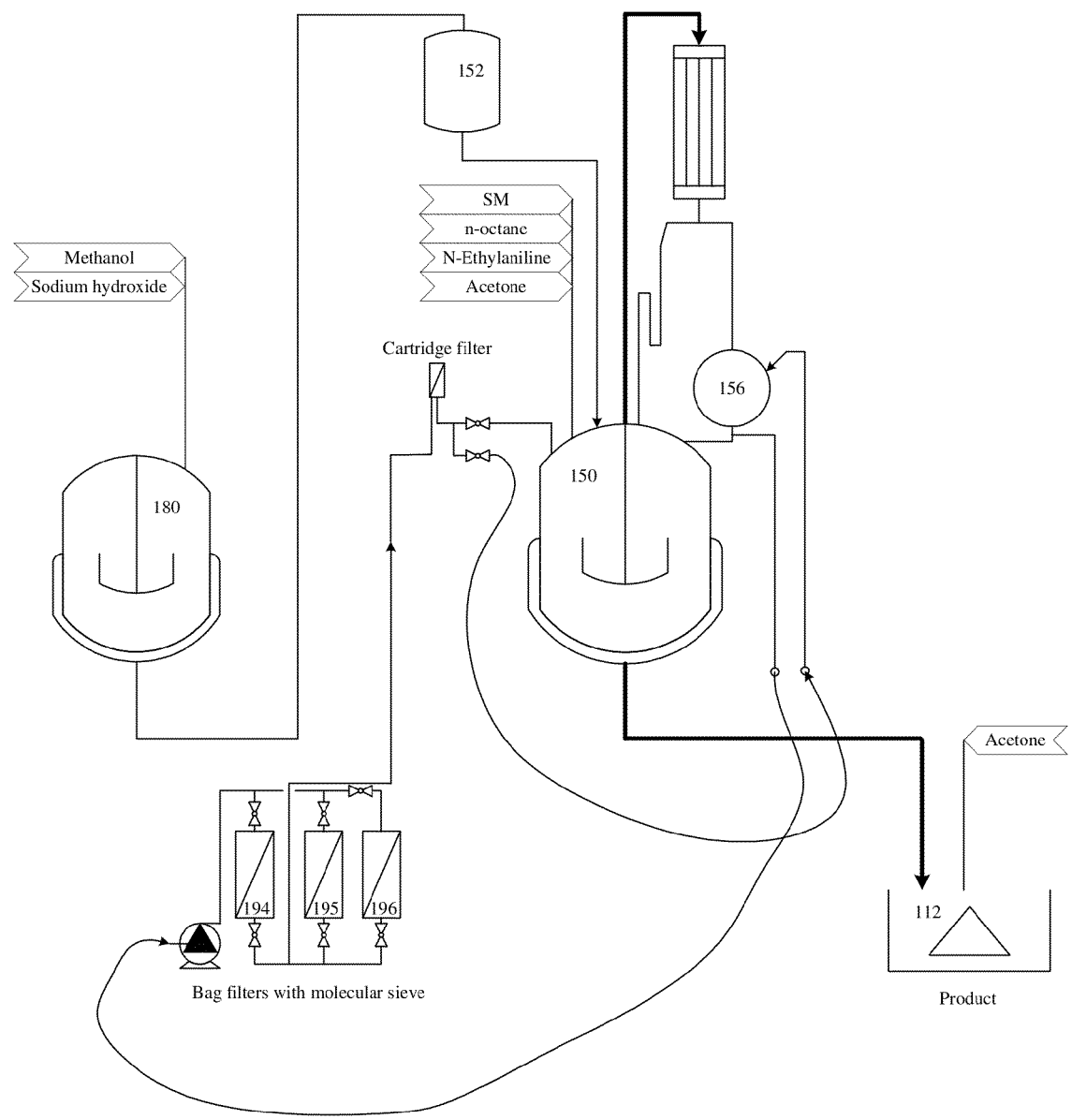
FIG. 2 represents an equipment set-up in pilot plant for production of Paquinimod.

The equipment set-up illustrated in FIG. 2 was used in a large-scale manufacturing of Paquinimod. A glass-lined reactor was charged with 4 (11.6 kg) through the manhole, followed by the addition of n-octane (212 kg) and n-ethyl aniline (13.4 kg). The mixture was heated to reflux temperature, i.e. 125° C. n-Octane was distilled off to a glass-sphere (156) at atmospheric pressure. The distillate in pos 156 was pumped through a bag filter (194) filled with 4 A molecular sieves (7.5 kg), when the volume had become 70 L. The distillation was continuous during the operation. The distillate was re-circulated back to the reactor as well as to the glass sphere to allow a continuous flow through the filter. After 7 hours the mixture was cooled to ≤60° C. An in process control (IPC) was withdrawn to check the conversion according to actual specification. Immediately after the sampling the mixture was heated to reflux temperature. Distillation and re-circulation through a second bag filter (195) filled with molecular sieve (7.5 kg) were continued. Since the first sample was not approved a second sample was withdrawn after additional 4.5 hours of re-circulation. Sample no. 2 was approved according to the specification. The results are presented in the Table 2.

TABLE 2

| IPC results. | | | |
|---|---|---|---|
| Sample | IPC analysis | Criteria (%) | Result (%) |
| 1 (7 hours) | Starting material 4 | ≤2 | 8.6 |
| 2 (11.5 hours) | | | 1.3 |

Additional distillation and re-circulation through a third bag filter (196) filled with molecular sieve (7 kg) were started before the result of the IPC analysis was received. Since the result was approved the re-circulation was interrupted. Distillation was continued until a set volume (110±10 L) in the reactor.

In another campaign of manufacturing A using the prior art method a reactor was charged with 4 (6.3 kg), n-octane (124 kg) and n-ethyl aniline (6.9 kg). After distilling off 88 kg solvent during 16 hours IPC showed that 2.7% of 4 remained.

References Cited

U.S. Pat. No. 6,875,869
U.S. Pat. No. 5,912,349
U.S. Pat. No. 6,133,285
Jansson et al., J. Org. Chem. 2006, 71, 1658-1667
Lu Jin et al., J. Phys. Chem. A 2008, 112, 4501-4510

Wennerberg et al., Org. Process. Res& Dev. 2007, 11, 674-680
Jönsson et al., J. Med. Chem. 2004, 47, 2075-2088

The invention claimed is:
1. A method for preparing a compound of formula (I)

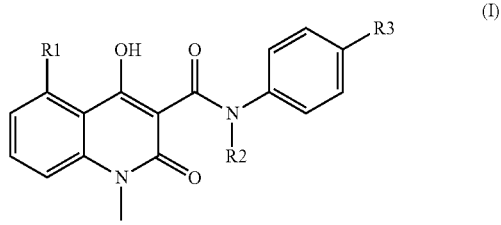
(I)

wherein,
R1 is ethyl, R2 is ethyl and R3 is H; or
R1 is chloro, R2 is ethyl and R3 is H; or
R1 is methoxy, R2 is methyl and R3 is trifluoromethyl; the method comprising:
(i) reacting a compound of formula (II)

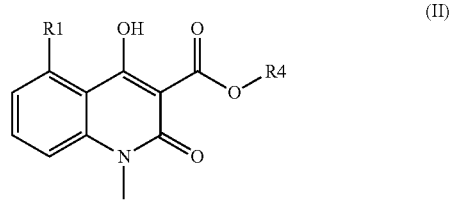
(II)

wherein,
R1 is ethyl, chloro or methoxy; and
R4 is C1-C4 alkyl;
with a compound of formula (III)

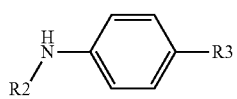
(III)

wherein,
R2 is ethyl and R3 is H; or
R2 is methyl and R3 is trifluoromethyl;
in a refluxing mixture containing an aliphatic solvent or a mixture of aliphatic solvents, said aliphatic solvent(s) having a boiling point in the range of 68-191° C.;
(ii) condensing vapors of the refluxing mixture;
(iii) treating the condensed vapors with an alcohol scavenging agent selected from molecular sieves or with an alcohol scavenging agent which is a mixture of molecular sieves, to remove an alcohol byproduct (R4OH) from the condensed vapors; and
(iv) returning the treated condensed vapors free of the removed R4OH back to the reaction mixture.

2. The method according to claim 1, wherein the aliphatic solvent(s) have a boiling point in the range of 80-150° C.
3. The method according to claim 1, wherein the aliphatic solvent(s) have a boiling point in the range of 95-130° C.
4. The method according to claim 1, wherein the alcohol scavenging agent is selected from 3A, 4A, 5A, 13X molecular sieves or is a mixture of any of said molecular sieves.
5. The method according to claim 1, wherein the aliphatic solvent(s) is/are selected from C6-C10 branched or linear alkanes and cycloalkanes.
6. The method according to claim 1, wherein the aliphatic solvent(s) is/are selected from C7-C8 branched or linear alkanes and cycloalkanes.
7. The method according to claim 6, wherein the aliphatic solvent(s) is/are selected from n-heptane, n-octane, methylcyclohexane, 2,2,4-trimethylpentane and cyclooctane.
8. The method according to claim 7, wherein the aliphatic solvent(s) is/are selected from n-heptane and n-octane.
9. The method according to claim 1, wherein R4 is selected from methyl, ethyl, n-propyl, iso-propyl and n-butyl.
10. The method according to claim 9, wherein R4 is selected from methyl and ethyl.
11. The method according to claim 1, wherein
R1 is ethyl, R2 is ethyl, R3 is H, R4 is methyl or ethyl;
the alcohol scavenging agent is a 3A, 4A, 5A or 13X molecular sieve, or is a mixture thereof; and
the aliphatic solvent(s) is/are selected from n-heptane and n-octane.
12. The method according to claim 1, wherein
R1 is chloro, R2 is ethyl, R3 is H, R4 is methyl;
the alcohol scavenging agent is a 3A, 4A, 5A, or 13X molecular sieve; and
the aliphatic solvent(s) is/are selected from n-heptane and n-octane.
13. The method according to claim 1, wherein
R1 is methoxy, R2 is methyl, R3 is trifluoromethyl, R4 is methyl or ethyl;
the alcohol scavenging agent is a 3A, 4A, 5A or 13X molecular sieve, or is a mixture thereof; and
the aliphatic solvent is n-octane.
14. The method according to claim 2, wherein the aliphatic solvent(s) is/are selected from C6-C10 branched or linear alkanes and cycloalkanes.
15. The method according to claim 3, wherein the aliphatic solvent(s) is/are selected from C6-C10 branched or linear alkanes and cycloalkanes.
16. The method according to claim 4, wherein the aliphatic solvent(s) is/are selected from C6-C10 branched or linear alkanes and cycloalkanes.
17. The method according to claim 2, wherein the aliphatic solvent(s) is/are selected from C7-C8 branched or linear alkanes and cycloalkanes.
18. The method according to claim 3, wherein the aliphatic solvent(s) is/are selected from C7-C8 branched or linear alkanes and cycloalkanes.

* * * * *